United States Patent [19]
Keely

[11] 4,428,370
[45] Jan. 31, 1984

[54] INSERTION UNIT FOR A VAGINAL DIAPHRAGM

[76] Inventor: Patricia G. Keely, 15500 Chispa Rd., Atascadero, Calif. 93422

[21] Appl. No.: 346,514

[22] Filed: Feb. 8, 1982

[51] Int. Cl.³ .............................................. A61F 5/46
[52] U.S. Cl. .................................................... 128/127
[58] Field of Search ............................. 128/127–131; 604/14, 15, 18, 55, 16

[56] References Cited

U.S. PATENT DOCUMENTS

| | | | |
|---|---|---|---|
| 2,141,040 | 12/1938 | Holt | 128/127 |
| 2,324,485 | 7/1943 | Chamberlain, Jr. | 128/127 |
| 2,714,886 | 8/1955 | Castelli | 128/127 |
| 3,674,026 | 7/1972 | Werner et al. | 604/14 |

Primary Examiner—Henry J. Recla
Assistant Examiner—Karin M. Reichle
Attorney, Agent, or Firm—Harvey G. Lowhurst

[57] ABSTRACT

An insertion unit for a vaginal diaphragm which is formed of a hollow tubular member with a plurality of flexible segments integral with the forward end to define an opening if flexed outwardly. A movable piston in the tubular member which holds the diaphragm in a lengthwise folded position and which, when the tubular member is withdrawn rearwardly, flexes the segments outward, to allow the diaphragm to move out of the tubular member and spring into position in the vaginal canal.

5 Claims, 9 Drawing Figures

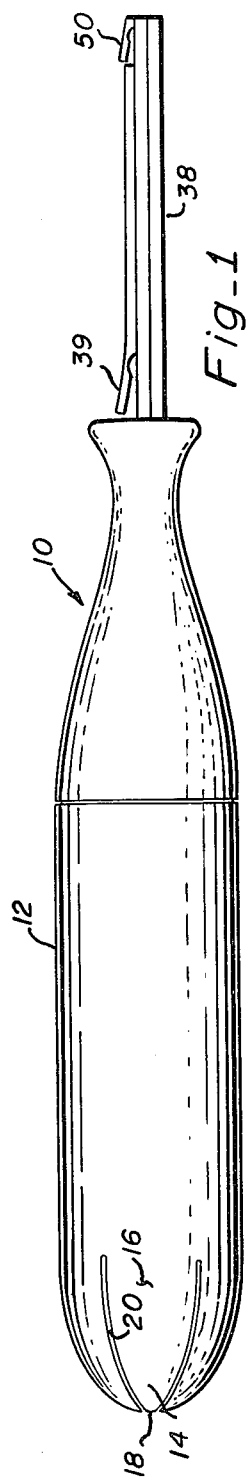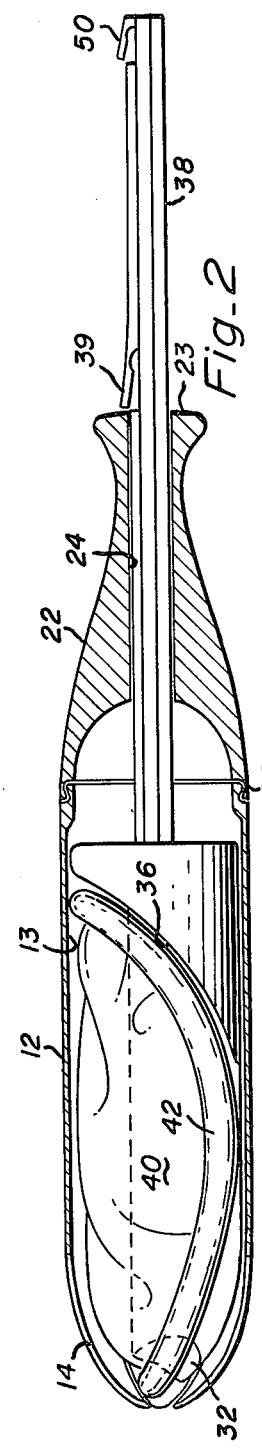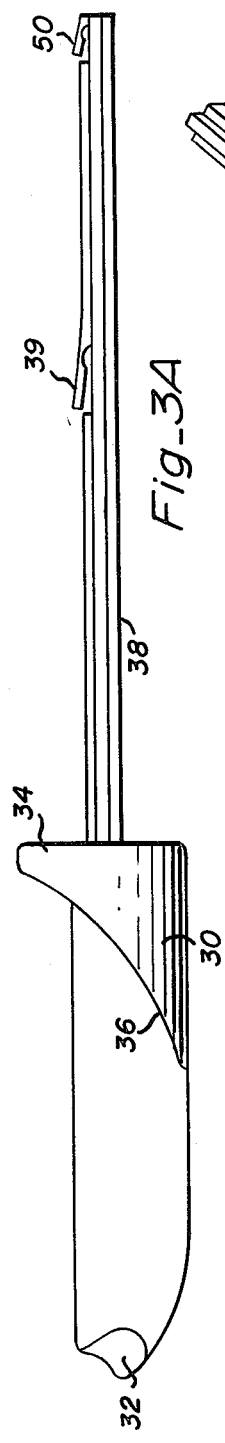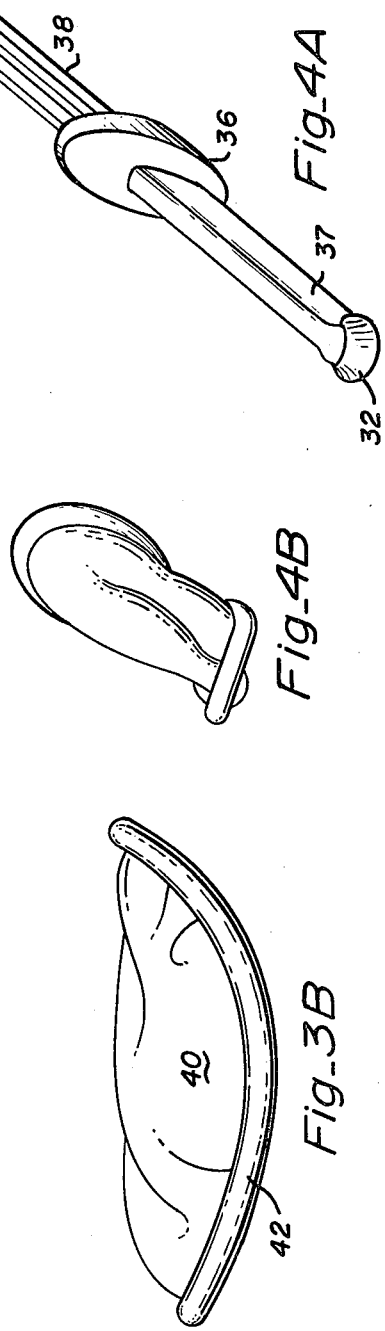

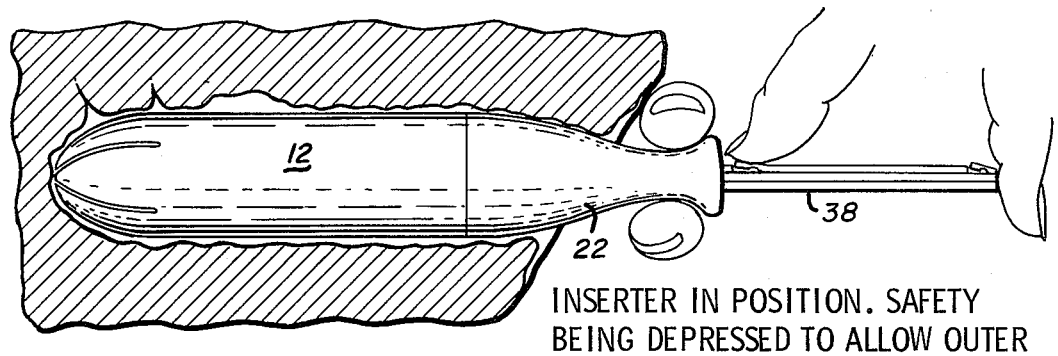
Fig_5A  INSERTER IN POSITION. SAFETY BEING DEPRESSED TO ALLOW OUTER SLEEVE WITHDRAWAL
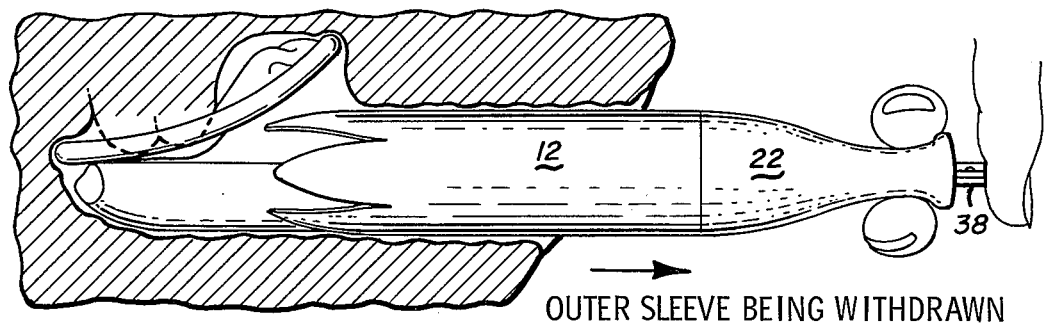
Fig_5B  OUTER SLEEVE BEING WITHDRAWN
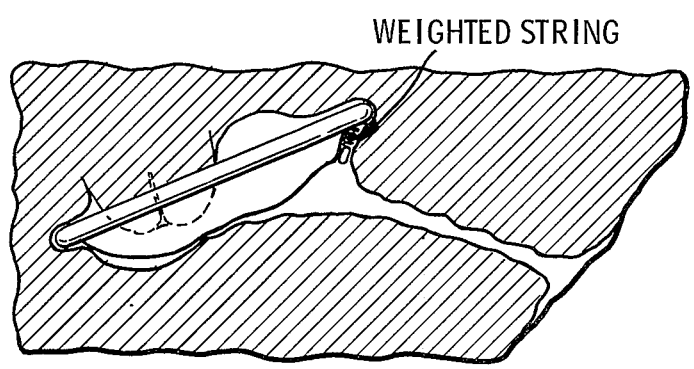
Fig_5C  WEIGHTED STRING

INSERTION UNIT FOR A VAGINAL DIAPHRAGM

BACKGROUND OF THE PRESENT INVENTION

This invention relates to contraceptive diaphragms, and more particularly to an insertion unit for such a diaphragm.

Due to the undesirable side effects to the user of the orally administered birth control pills, for the suppression of conception, there has been a continued search for acceptable alternate methods of birth control. Another more recent alternative to birth control pills is the intra-uterine device which, even though having been found effective to prevent conception, has been found not always easily tolerated by the tissues and mucous membrane in the uterus, causing deterioration or dislodgement.

Because of these deficiencies, there has been renewed interest in the well known diaphragm as a method of preventing contraception whereby a flexible, non-permeable membrane is lodged crosswise in the vaginal canal at the base of the cervix, and is retained in this position by virtue of the surrounding contractile wall tissue. The diaphragm probably never reached its full potential as a valuable method of birth control primarily because the issue of convenience in its insertion and removal has never been adequately addressed by either the prescribing physician or the pharmaceutical manufacturers. There are a number of disadvantages associated with the insertion of the diaphragm which have contributed to its use falling in disfavor with the advent of the pill and the intra-uterine device. One of these is the correct placement or proper positioning of the diaphragm in the vagina so it covers the end of the cervix to prevent insemination. Another is the necessity of applying a spermicidal jelly to the interior rim of the diaphragm prior to insertion, which is often messy and unesthetic and the actual interruption of the spontaneous sexual behavior is apt to produce a cooling, and diminishing interest or passion. Such a delay can even contribute to impotency or loss of erection for the male with all of its subsequent psychological reaction. Finally, there are individuals who are more comfortable inserting the diaphragm with some type of applicator instrument instead of by hand because the necessary application of spermicidal jelly causes the diaphragm to be difficult to control, and may cause improper and/or time consuming placement.

OBJECTS OF THE INVENTION

It is therefore an object of the present invention to provide an insertion unit for a vaginal diaphragm which houses a diaphragm already having spermicidal jelly applied thereto, which is easily insertable into the vaginal canal, and which allows expulsion of the diaphram from the housing into the proper position by the use of a plunger.

It is a further object of the present invention to provide a diaphragm insertion unit combination which is in the form of a package insertable into the vaginal canal and which allows proper placement of this diaphragm when the insertion unit is withdrawn.

It is a further object of the present invention to provide an insertion unit for a diaphragm which can be loaded with a diaphragm prior to insertion and use.

It is also an object of the present invention to provide a package containing an insertion unit as well as a diaphragm with both, or at least the diaphragm, being disposable after one use.

BRIEF SUMMARY OF THE INVENTION

The insertion unit is formed of a hollow tubular member which is closed at the forward end with plurality of triangular flexible segments having adjacent sides in substantially touching contact. The hollow tubular member houses a slidable piston member which includes means to engage and to hold the normally flexible rim of the diaphragm when urged into its lengthwise folded position by the interior surface of the tubular handle or rod which passes out of the rear end of the hollow tubular member and which, if pushed forwardly, moves the piston member together with the diaphragm through the triangular flexible segments out of the tubular member and into proper position in the vagina covering the cervix.

BRIEF DESCRIPTION OF THE DRAWINGS

FIG. 1 is a side view of the insertion unit of the present invention with the diaphragm being stored inside thereof;

FIG. 2 is a cross section view of the hollow tubular member of FIG. 1 showing a side view of the housed piston member and the lengthwise folded diaphragm;

FIG. 3A is a side view of the piston member as shown in FIG. 2, and FIG. 3B is a like view of the lengthwise folded diaphragm separated from the piston member;

FIG. 4A is a perspective view, taken from the front and above the piston member shown in FIG. 3A, and FIG. 4B is a like view of the lengthwise folded diaphragm separated from the piston member; and FIGS. 5A, 5B, and 5C are progressive side views showing the insertion of the insertion unit of the present invention in the vagina, with FIG. 5A showing full insertion of the unit, FIG. 5B showing the tubular housing being retracted while the piston member retains the diaphragm in position and the lengthwise folded diaphragm being expulsed from the piston member into place, and FIG. 5C showing the contraction of the vagina to its normal diameter width with the diaphragm now properly in place over the cervix.

DETAILED DESCRIPTION OF THE DRAWING

Referring now to the drawing, and particularly to FIGS. 1 through 4 thereof, there is shown the insertion unit 10 comprising a hollow tubular member 12 which includes, at its forward end, a plurality of substantially triangular flexible segments 14 intergral at their respective basis 16 with the forward end of tubular member 12 and have their respective apexes 18 converging forwardly to a point and having respective adjacent sides 20 in substantially touching contact. The triangular flexible segments 14 are biased to close the forward end of tubular member 12. At the rear end of tubular member 12 is a disconnectable rearward portion 22 which includes an opening 24 and snap connection means 26 for attachment to the main body portion of member 24.

Disposed within hollow tubular member 12 is a movable piston 30 which includes a forwardly and upwardly facing open channel 32 at its forward end and a cylindrical rear portion 34 which slidingly engages the peripheral interior surface 13 of tubular member 12 and which has a forwardly and upwardly curving seat 36. Disposed at rear portion 34 of piston member 30 is a handle 38 which includes an outwardly biased and inwardly depressible detent 39 which is disposed, as best in FIG. 1, to bear against face 23 of rearward portion 22.

Forward channel 32 and rearward seat 36 of piston member 30 are separated by a center portion 37 in such a manner that a diaphragm 40 having a stiff resilient rim 42, is accommodated on piston member 30 such that the forward end of diaphragm rim 42 is seated in channel 32 and the rear end of diaphragm rim 42 lies on seat 36 when diaphragm 40 is held in its lengthwise folded position by the interior surface of member 12, as best seen in FIG. 2.

The diaphragm, as best shown in FIG. 4B, is placed in its lengthwise folded position on a piston member 30 within tubular member 12 to form a package as best seen in FIG. 2. As a practical matter, the diaphragm (particularly if disposable) could be prepackaged in insertion unit 12 for purchase by the user in which case the interior surface of the diaphragm would normally be provided with a spermicidal substance. As an alternative, a user may insert the diaphragm to be used by placing it on piston member 30 after first disconnecting rear end 22 at snap 26 and thereafter pushing the diaphragm loaded piston member into tubular member 12. The rear opening is closed by snapping rear end 22 again into place.

If the inserter is to be re-usable, it should be made of moderate to heavy weight plastic that is designed for durability and re-use to allow for the insertion of a regular re-usable diaphragm which is loaded into the inserter by the user prior to insertion. The inserter is of such strength and durability that it can be cleansed and re-used at later dates.

Conversely, by utilizing a less durable and lighter weight plastic material, the unit can be constructed for one-time use only. Such a disposable unit would be utilized in conjunction with a light weight disposable diaphragm which is loaded into the inserter by the manufacturer, and which can be marketed as a two piece disposable ensemble.

In operation, the user takes package 10 and inserts it into the vaginal canal, as best shown in FIG. 5A, until point 18 rests against the anterior fornix at the end of the canal. As the outer sleeve is withdrawn, the remainder of the diaphragm will spring into place against the posterior fornix, thus creating a cover over the entire cervix. The user then grabs end portion 22 with two fingers of one hand, and with another finger depresses detent 39 while at the same time withdrawing tubular member 12 rearwardly causing piston member 30 to remain stationary and the opening of triangular flexible segments 14 as tubular member 12 is retracted thereby allowing diaphragm 40, as best seen in FIG. 5B, to leave insertion unit 10 and to snap in place over the cervix. Another detent 50 is provided, very similar to detent 39, which will bear against face 23 when the tubular member is retracted a sufficient distance to allow the diaphragm to be expelled into place. The final position of the diaphragm 40 is shown in FIG. 5C with the vagina contracted to In another embodiment of the present a weighted string may be provided which facilitates the removal of the diaphragm after use. The string is constructed of cotton fibres or similar materials which may be folded in such a manner as to allow for spontaneous expansion when contacted by fluids or significant moisture. The string is connected to the diaphragm by means of a weave which encompasses the circumference of the diaphragm. In addition, the string is wighted at its free end with a material similar to surgical weights commonly used in bronchostomy tubes, and said weight is contained within a pouch of some inert material. The string is designed to remain folded against the perimeter of the diaphragm during insertion, and the weight in conjunction with vaginal fluids and moistures acting on the pleated string cause the string to expand and drop down within the vaginal vault, within easy reach of the user, facilitating simple removal of the device.

What is claimed is:

1. An insertion unit for a vaginal diaphragm having a stiff resilient rim therearound, said diaphragm having a forward portion, a rearward portion and side portions when folded lengthwise, said insertion unit comprising:

a hollow tubular member having a forward end and a rearward end;

a plurality of substantially triangular flexible segments integral at their respective bases with the forward end of said tubular member and having their respective apexes converging forwardly to a point and having adjacent sides in substantially touching contact to close the forward end of said tubular member and, upon being flexed outwardly, to define an opening having a diameter substantially equal to the internal diameter of said tubular member;

a movable piston member slidably mounted within said tubular member for holding said diaphragm in a lengthwise folded position and to expel said diaphragm from the forward end of said tubular member through said segments, (a) said piston member including a forward portion, a rearward portion, and a center portion for connecting said forward and said rearward portions, said forward portion of said piston member having means for engaging the forward portion of the rim of the lengthwise folded diaphragm, (b) the rearward portion of said piston member slidingly engaging the interior surface of said tubular member and defining a curved seat for engaging and supporting the rear portion of the rim of the diaphragm said curved seat extending longitudinally and circumferentially along said piston from a point where the rearward portion engages the interior surface of said tubular member to a point on the opposite side of said piston within said center portion, said means for engaging the forward portion of said rim being aligned with said seat such that when said folded diaphragm is mounted on said piston, the side portions of said diaphragm overlaps said piston with the forward portion held by said engaging means and the rearward portion supported by said seat; and a handle mounted on the rearward portion of said piston member and extending beyond said tubular member for moving said piston member through said flexible segments to expel the diaphragm.

2. An insertion unit in accordance with claim 1 in which the forward end of said piston member includes a forwardly facing open channel dimensioned to accomodate the forward portion of the rim of the diaphragm.

3. An insertion unit in accordance with claim 2 in which said forwardly facing open channel also faces upwardly to facilitate the upward disengagement of the diaphragm upon expulsion.

4. An insertion unit in accordance with claim 1 in which said tubular member haVing a disconnectable rearward portion mounted on the rearward end of said tubular member to close the rearward end of said tubular member, and in which said rearward portion includes an opening for slidingly supporting said handle.

5. An insertion unit in accordance with claim 4 in which said handle includes a normally outwardly biased and depressible safety stop to prevent forward movement of said handle unless said safety stop is depressed, said safety stop being located to bear against the rearward portion of said tubular member when said handle is fully retracted.

* * * * *